United States Patent
Wang et al.

(10) Patent No.: US 6,430,513 B1
(45) Date of Patent: *Aug. 6, 2002

(54) MONITORING CONSTITUENTS OF AN ANIMAL ORGAN USING STATISTICAL CORRELATION

(75) Inventors: Yongdong Wang, Wilton; David H. Tracy; Paul G. Saviano, both of Norwalk, all of CT (US); Alan M. Ganz, Scarsdale, NY (US); Koichi Nishikida, Newtown; Gitesh Kumar, Norwalk, both of CT (US)

(73) Assignee: PerkinElmer Instruments LLC, Shelton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/479,642

(22) Filed: Jan. 7, 2000

Related U.S. Application Data

(63) Continuation of application No. 09/385,248, filed on Aug. 28, 1999, now abandoned.
(60) Provisional application No. 60/099,098, filed on Sep. 4, 1998.

(51) Int. Cl.[7] .............................................. G01N 31/00
(52) U.S. Cl. ...................... 702/28; 33/1 B; 250/339.03; 600/310; 600/323; 600/328; 600/344; 600/473; 356/39; 702/19
(58) Field of Search .......................... 702/28, FOR 131, 702/FOR 139; 600/323, 324, 328, 344, 310; 128/633, 634; 250/339.01, 339.07, 341.1; 356/39–41, 317–319, 323

(56) References Cited

U.S. PATENT DOCUMENTS

| | | | | |
|---|---|---|---|---|
| 4,223,680 A | * | 9/1980 | Jobsis | 600/344 |
| 4,281,645 A | * | 8/1981 | Jobsis | 600/344 |
| 4,321,930 A | * | 3/1982 | Jobsis et al. | 600/344 |
| 4,380,240 A | * | 4/1983 | Jobsis et al. | 600/344 |
| 4,630,375 A | * | 12/1986 | Spolyar | 33/1 B |
| 4,805,623 A | * | 2/1989 | Jobsis | 600/328 |
| 5,122,974 A | * | 6/1992 | Chance | 600/323 |
| 5,386,827 A | * | 2/1995 | Chance et al. | 600/310 |
| 5,664,574 A | * | 9/1997 | Chance | 600/473 |
| 5,706,208 A | * | 1/1998 | Osten et al. | 702/19 |
| 5,729,333 A | | 3/1998 | Osten et al. | 356/39 |
| 5,900,632 A | * | 5/1999 | Sterling et al. | 250/339.03 |
| 6,195,574 B1 | * | 2/2001 | Kumar et al. | 600/323 |

OTHER PUBLICATIONS

Yunsong Yang, Hanli Liu, Xingde Li, Britton Chance/ Low–Cost Frequency–Domain Photon Migration Instrument for Tissue Spectroscopy, Oximetry, and Imaging/ May, 97 / 1562–1569.

H.Y. Ma, C.,W. Du and B. Chance/ "A Homodyne Frequency–Domain Instrument—I&Q Phase Detection System"/ May, 97/ 1–12.

* cited by examiner

Primary Examiner—John S. Hilten
Assistant Examiner—John Le
(74) Attorney, Agent, or Firm—St. Onge Steward Johnston & Reens LLC

(57) ABSTRACT

Constituents such as oxy- and deoxy-hemoglobin are monitored non-invasively in an animal organ such as a brain with a spectrometric instrument by passing radiation through the organ. Concentrations are computed from the spectral intensities and from a statistical correlation model. To predetermine the correlation model, the procedures are effected for a plurality of organs of a same type with each organ having established concentrations of the selected constituents, and the correlation model is statistically determined from the concentrations and corresponding intensities. For more accuracy computations are normalized to path length which may be determined by utilizing several discrete wavelengths with RF modulations.

28 Claims, 7 Drawing Sheets

MONITORING CONSTITUENTS OF AN ANIMAL ORGAN USING STATISTICAL CORRELATION

This application is a continuation of U.S. application Ser. No. 09/385,248, filed Aug. 28, 1999, now abandoned, which claims the benefit of U.S. Provisional Application No. 60/099,098 filed Sep. 4, 1998. This invention relates to monitoring constituents in an animal organ, particularly oxygenated and deoxygenated hemoglobin in a brain.

BACKGROUND

There has been a desire for an instrument to monitor constituents in an animal or human organ non-invasively. A particular example is monitoring of oxygen level in the brain which is particularly important, for example during surgery, where a significant number of patients come out of the anesthesia with various degrees of and sometimes permanent brain function deficiency. It is believed that in a significant portion of such cases, lack of sufficient oxygen to the brain is the cause of such deficiencies. Thus, the ability to accurately monitor oxygen level in the brain directly, rather than through indirect methods such as a pulse oximeter placed on another portion of the body, would have obvious advantages including non-invasiveness, immediate and timely results, and relative simplicity. Techniques to achieve such monitoring have involved passing near-infrared radiation through a cranium and analyzing the modified output radiation.

One known method is to pass radiation having several discrete wavelengths from laser diodes equal in number to the number of constituents to be measured, for example two wavelengths for oxygenated and deoxygenated hemoglobin. The radiation is modulated with radio frequency. The output modified by the brain is used to calculate changes in amplitude and phase which lead to determination of absorption coefficients at the different wavelengths. Simultaneous equations with these coefficients determine concentrations of the constituents of interest and the oxygen saturation which is the percentage of oxygenated to total hemoglobin.

Another method is to utilize continuous-wave radiation, in which output from a detector on a cranium is spectrally analyzed to yield oxygen saturation. Although a full spectrum is used, the analysis is based on modeling with either a small number of wavelengths or a few known constituents such as the oxy and deoxy hemoglobin and water.

Any such monitoring encounters difficulties resulting from the biological complexities of an organ such as a brain, compared with spectrometric instrumentation that ordinarily analyzes fluids that are readily probed, contained or flowing in a tube suitable for the instrument. Geometries of different subjects vary considerably and variations occur even within an individual. Further, tissues are not uniform. The radiation is scattered so that a path is not well defined. Signal to noise ratios for infrared radiation through solid material are generally low. Current methods for monitoring of craniums depend on theoretical or mathematical models that may be oversimplified or inaccurate. Thus there is a need for better accuracy and reproducibility.

Consequently, an object of the invention is to provide a novel method and means for monitoring constituents in an animal organ non-invasively, particularly oxygenated and deoxygenated hemoglobin in a brain.

SUMMARY

The foregoing and other objects are achieved by a method or an apparatus for monitoring one or more selected constituents in an animal organ, with a spectrometric instrument that includes a source of an input beam of infrared radiation having a substantially full spectrum in a spectral range that includes absorbance wavelengths of the selected constituents, and a spectral detector receptive of such radiation to generate representative signal data. The instrument may be, advantageously, an infrared Fourier transform spectrometric instrument. The input beam is directed into an animal organ such that the radiation is attenuated by constituents of the organ including the selected constituents. The spectral detector is positioned so as to be receptive of the attenuated radiation from an exit site from the organ so as to generate signal data representative of spectral distribution of the attenuated radiation. Spectral intensities are calculated over the spectral range from the signal data. Concentrations of the selected constituents are computed from the spectral intensities and from a predetermined statistical correlation model relating such concentrations and spectral intensities. Advantageously the radiation is passed through a cranium such that the radiation is attenuated by brain constituents, particularly oxygenated hemoglobin and de-oxygenated hemoglobin, utilizing a spectral range from about 700 nm to about 1100 nm. Saturation level of oxygenated hemoglobin may be computed relative to a total of the oxygenated hemoglobin and de-oxygenated hemoglobin, whereby the saturation level is independent of path length of the radiation to the spectral detector.

To predetermine the correlation model, the foregoing procedures may be effected for a plurality of organs of a same type with each organ having established concentrations of the selected constituents, and the correlation model is statistically determined from the concentrations and corresponding intensities.

Intensities are preferably converted to absorbances, the concentrations being computed from the correlation model and the absorbances. For more accurate computation of concentrations, path length of the radiation is ascertained in the organ between the input site and the exit site, and each absorbance for each spectral increment is divided by the path length to effect normalized absorbances, the concentrations being computed from the correlation model and the normalized absorbances. To ascertain path length, a further beam of input discrete radiation comprises at least one discrete wavelength component in the spectral range, each wavelength component being modulated with a radio frequency signal. The further beam is directed into the organ at the input site such that the discrete radiation is modified by the organ. A radiation detector is positioned to be receptive of the modified radiation from the exit site so as to generate corresponding detector signals. A phase shift is determined between the radio frequency signal and the corresponding signals, and thereby between the input discrete radiation and the modified radiation for each discrete wavelength. From each phase shift, correspondingly at least one effective path length of the discrete radiation is calculated in the organ between the input site and the exit site. From each effective path length, a spectral path length is computed for each spectral increment in the spectral range. Each absorbance for each spectral increment is divided by the increment path length for that spectral increment to effect the normalized absorbances.

DETAILED DESCRIPTION

Figure 1:
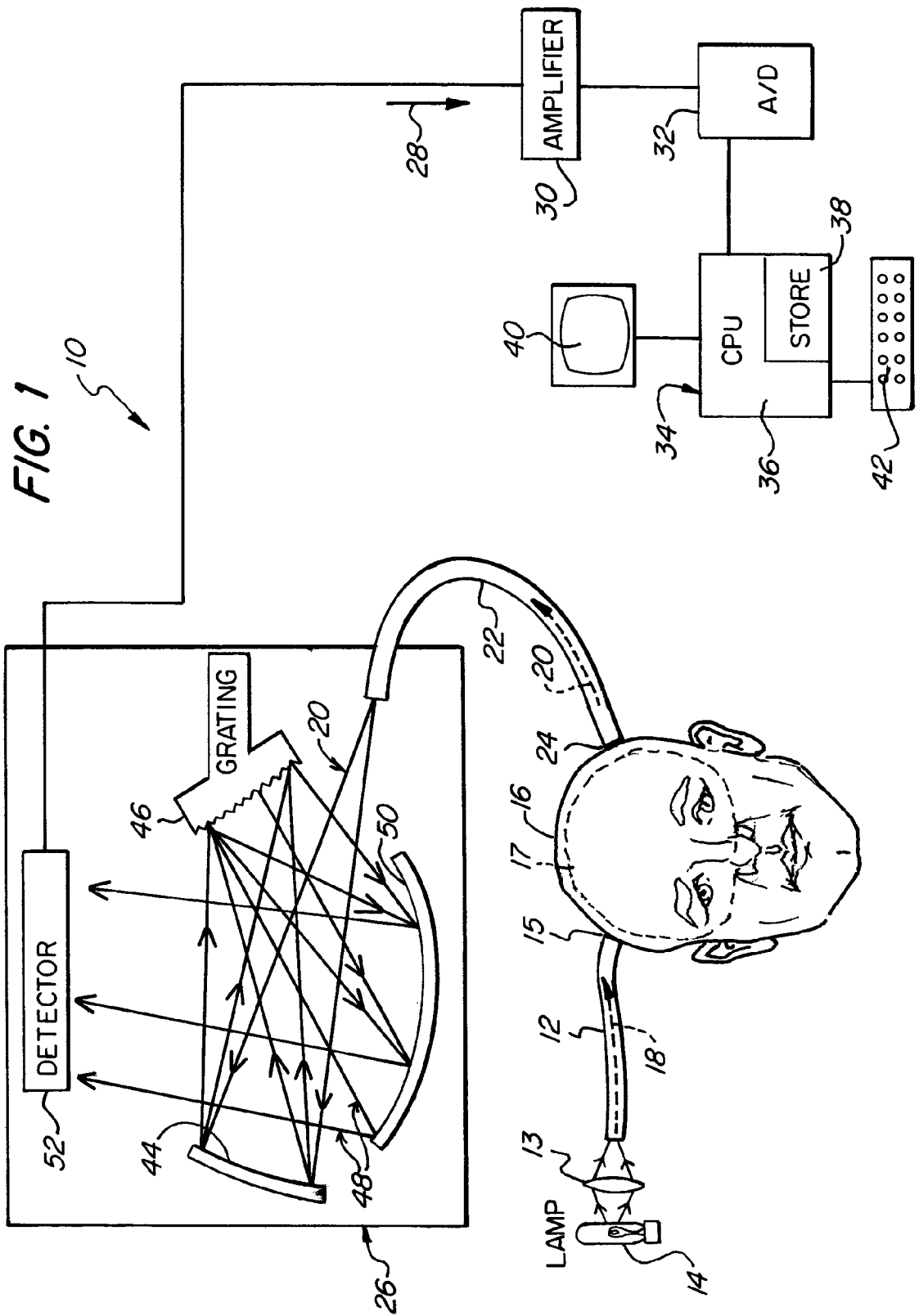
FIG. 1 is a diagram of a system in accordance with the invention.

A system 10 (FIG. 1) of the invention is directed to passing a beam 18 of infrared radiation from a light source 14 through a lens 13 into an input site 15 of a body part of an animal, for example the cranium 16 of a dog or a human being, so as to monitor one or more selected constituents in an organ such as a brain 17. The system is adapted for a living organ that is either in place or temporarily shifted or removed but still connected to the animal during surgery. The constituents may be bimolecular compounds, the system being particularly useful for monitoring oxygenated ("oxy") hemoglobin and deoxygenated ("deoxy") hemoglobin. The body part may be, for example, an external arm, foot, finger or the like, and the organ may be, for example, a brain, colon, liver, gall bladder, etc. The system and method of the invention is especially advantageous where the body part is a cranium which herein means a skull with brain and overlying skin and perhaps hair, and the organ examined is a brain. A fiber optic carrier 12 formed of an optical fiber or preferably a bundle of fibers, e.g. 6 mm diameter, is convenient for conveying the input beam to the cranium and brain, or other organ, which modifies the radiation by absorption and scattering. Alternatively, the input beam may be focused on the cranium directly without a fiber.

A second, similar fiber carrier 22 may be used to pick up attenuated radiation 20 exiting the cranium (or other organ) from a suitable point or site 24, for example about 5 cm from the input site. The second, output fiber carrier conveys the attenuated radiation to a spectral detector 26 to generate corresponding signal data 28 representative of spectral distribution of the attenuated radiation. Alternatively the detector may be positioned proximate the scull without a second fiber carrier. The signal data are amplified 30 and fed through an analog/digital (A/D) converter 32 to a computer 34 that typically includes a data processor (CPU) 36, disk and RAM storage 38, a monitor 40 for display and a keyboard 42 for operator input.

The spectral range is selected for suitability of the radiation passing through the organ with sufficient attenuation by absorption by the selected constituents without excessive interference by other constituents. Oxy and deoxy hemoglobin molecules have respective absorption peaks at about 920 nm and 760 nm which are separated from a strong water peak at about 975 nm. For these peaks it was determined that a spectral range of about 700 nm to 1100 nm is suitable for hemoglobin. Other examples for monitoring or measurement are cytochrome-$aa_3$ oxidase at 840 nm, other forms of hemoglobin such as carboxy-hemoglobin, pH, and $CO_2$ partial pressure.

The radiation source 13, 14 and the spectral detector 26 in combination form a spectrometric instrument. The instrument must perform in the spectral range of interest and have sufficient precision and adaptability to the present purpose, and otherwise may be a conventional or other desired spectrometric instrument. One such instrument is a dispersion spectrometer such as a Perkin-Elmer Paragon™ 1000. This utilizes lamp 14 as a broad spectrum ("white") light source with the input beam 18 focussed by lens 13 into the input fiber carrier 12. Radiation 20 from the output fiber carrier 22 is directed into the spectrometer 26 that functions as a spectral detector. The spectrometer of the present example includes a first concave mirror 44 for focusing to a grating 46 that effects a spectrum 48, and a second concave mirror 50 for collimating the spectrum to an array photoreceptor 52 which typically is a CCD that, in conjunction with the A/D, effects the digital signal data for the computer.

Another suitable type of dispersion instrument (not shown) is a scanning instrument in which a spectrum is generated by a grating or prism that is rotated to function as a source to effect an input beam from a slit, the beam having a time varying is wavelength. A photodetector effects time-varying signal data associated with the attenuation.

Figure 2:
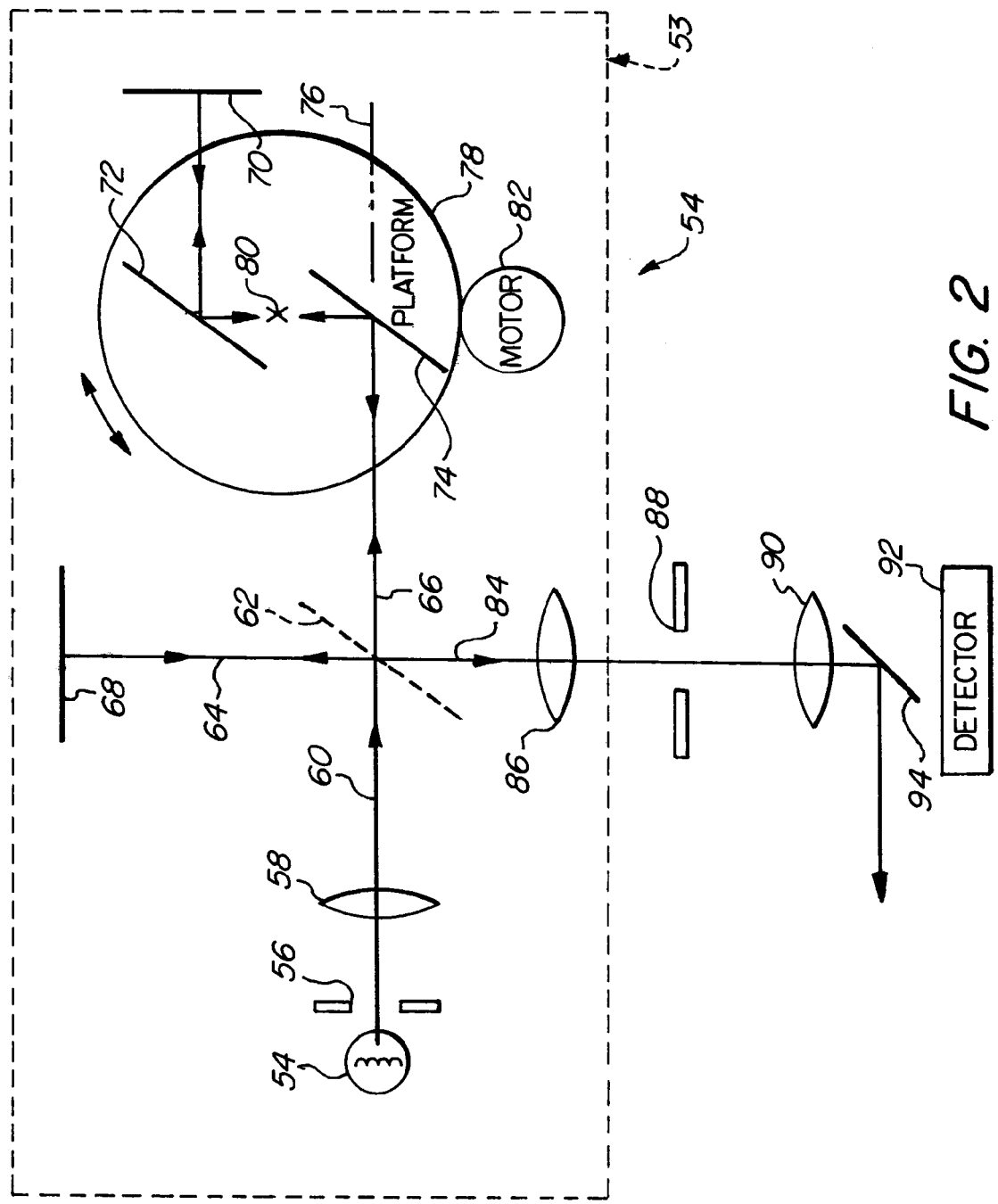
FIG. 2 is a schematic diagram of a portion of an apparatus for effecting the input beam of the apparatus of FIG. 1.

Preferably a Fourier transform infrared (FTIR) type of instrument 54 (FIG. 2) is used, such as a Perkin-Elmer System 2000 FTIR.

Such a spectrometric instrument substantially reduces effects of ambient radiation. In this case the "spectrum" in the form of a time-varying interference pattern is generated to effect the input beam prior to its being passed into the cranium. In the spectral light source 53, light radiation from a lamp 54 is transmitted through a source aperture 56 and continues through a collimator, such as a lens 58 or a mirror, and a combination of reflectors that constitute a conventional Michaelson interferometer. In this combination, the incoming white light beam 60 is split by a semi-reflective mirror 62 that reflects a first half 64 of the light beam and transmits the second half 66. The first beam 64 is reflected by a fixed mirror 68 back through the semi-reflector 62. The second beam 66, also reflected back, has a variable path length which may be accomplished in a simple system (not shown) by a movable second mirror to reflect back the semi-reflector. For better precision and alignment, the second mirror 70 is fixed but offset, and a pair of angled reflectors 72, 74 is interposed to reflect the second beam to and back from the offset mirror 70. The angled reflectors are mounted in parallel about 45° to the main light axis 76 on a platform 78 that is rotatable about an axis 80 centered between the mounted reflectors. The platform is connected directly or through its axle to a motor 82 that rotationally oscillates the orientation of the parallel reflectors over a range such as about 10° centering on the nominal 45°. The range setting may be under computer control. The number of oscillations in one data run is selected to provide sufficient spectral data, for example 16 cycles. The rotation varies the total path length of the second beam. The precise change in path length may be determined conventionally by a laser beam (not shown) interposed into the interferometer, or into another interferometer using the same pair of parallel reflectors, and counting nulls detected in the laser interference pattern (automatically by the computer if desired). Path length generally is changed up to about 10 mm in each oscillation.

Figure 3:
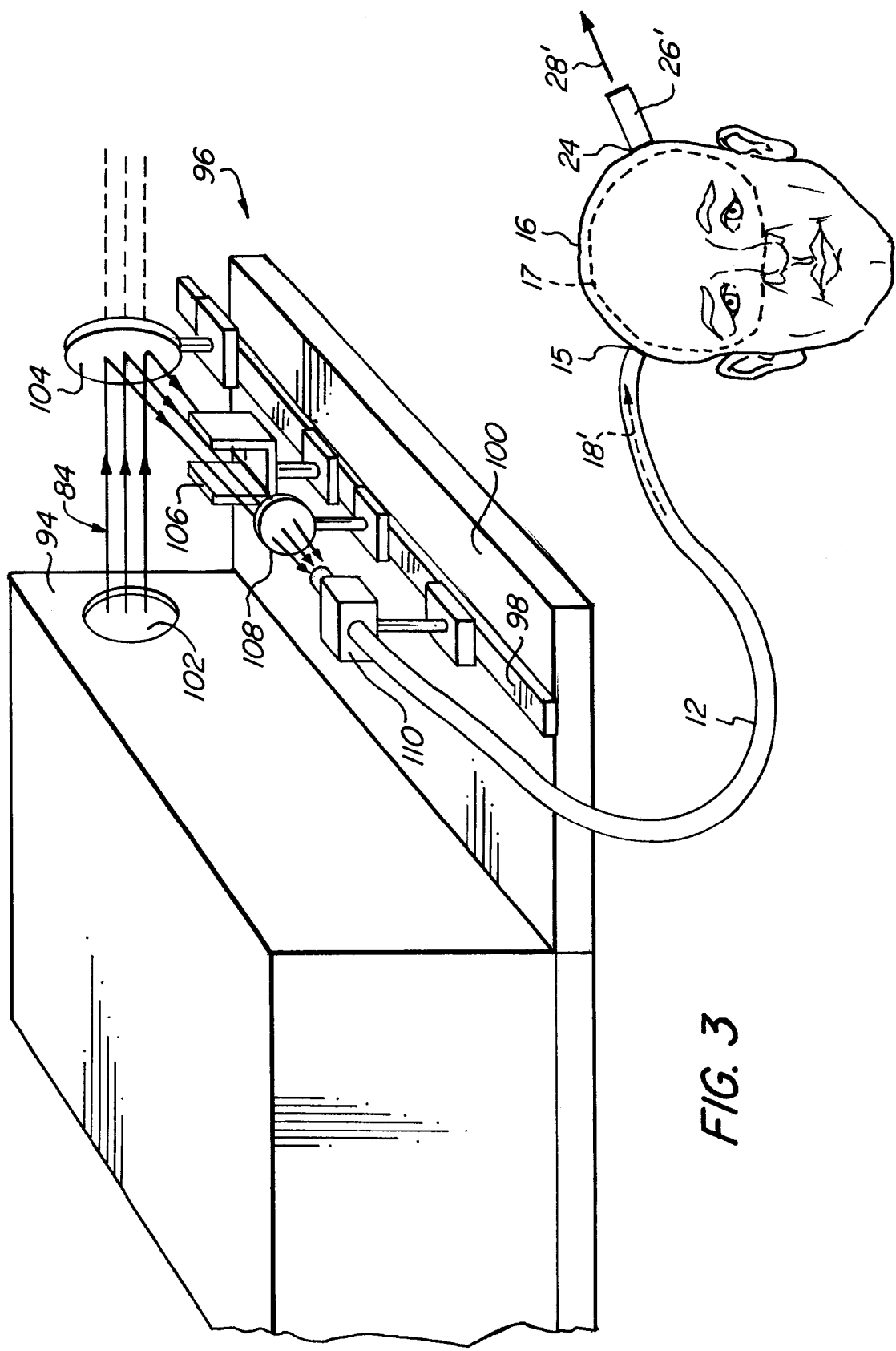
FIG. 3 is a perspective of a portion of the apparatus of FIG. 2.

A portion of the first beam 64 passes through the semi-reflector 62. A portion of the second beam 66 is reflected by the semi-reflector to combine with the first beam and thereby effect a time-scanned interference form of the spectral pattern 84 to be used as the input beam 18' (FIG. 3). The spectral beam may be folded if desired by one or more additional mirrors (not shown). The interference beam 84 is passed through a lens 86 which focuses the beam to a second aperture stop 88, known as a Jacquinot stop (J-stop). The lamp housing is aligned in all directions to fill the first aperture and provide a sharp image of the lamp wire at the J Stop and fill about 90% of the J-stop. The beam then is collimated by a further lens 90. A sample ordinarily placed adjacent to the J-stop is omitted, and the normal detector is removed, or the beam is reflected by a 45° mirror 94 away from the instrument detector 92 (which may be retained for diagnostics).

The FTIR instrument should be suitable for or adapted to handle the desired spectral range, e.g. 700 nm to 1100 nm. The lenses and beam splitter should be quartz for this infrared range, and full-reflection mirrors should be gold coated to reduce light loss. A replacement light source is a 100 watt quartz halogen bulb (e.g. model #6333 from Oriel Corporation, Stratford, Conn.) with a 4-element borosilicate crown lamp housing (e.g. Oriel model #66198), to avoid excessive heating. A neutral density filter should be used if necessary to change throughput experimentally or to provide a selected maximum light input into the cranium without significantly heating the brain, e.g. 38 mW from the fiber carrier. For a 6 mm diameter fiber carrier this corresponds to a light irradiance of 135 mW/cm$^2$, comparable to tropical solar irradiance. Both the source aperture and the J-stop aperture should be fully open, which reduces resolution but such a resolution (e.g. 64 cm$^{-1}$) should be adequate.

The foregoing FTIR instrument components are enclosed conventionally in a housing 94 (FIG. 3). An auxiliary optical train 96 mounted on a rail 98 on a platen 100 (which is attached to the housing) is added to direct the beam into the input fiber carrier 12. Radiation 84 exiting the housing from a hole 102 therein encounters a dichroic mirror 104 (e.g. Oriel model #57401) placed at 45° to the incident beam. The mirror operates in reflection as a band pass filter such that more than 90% of the desired wavelengths (700–1100 nm) are contained in the slightly convergent reflected beam. A filter holder 106 is provided for optional filtering or attenuation. Following the filter holder a lens 108 focuses the beam to the tip of the input fiber carrier 12 held in a positioner 110. The auxiliary train 96 may be contained in an enclosure (not shown) attached to the main instrument. Any other conventional or other desired optics may be utilized to pass the beam into the fiber carrier. The fiber carrier may be conventional, such as 1.8 m (6 ft) long, 6 mm diameter, made of borosilica glass for transmission 400–1400 nm. The input beam 18' of the time varying interference pattern is directed by the carrier into the input site 15 on the cranium 16.

The attenuated light from the exit site 24 may be received by an output fiber carrier which directs it to a detector. Alternatively (as shown) the second fiber carrier is omitted and the light goes directly to the detector 26'. Percentage loss in such a fiber carrier is about 50%, so it is desirable to apply the detector directly to the cranium, which is practical with FTIR. In either case, the corresponding spectral signals 28', which are time varying in response to the interferometer and attenuation, are amplified and digitized by an amplifier before being passed to the computer.

The spectral detector may be a standard FTIR detector, e.g. a triglycine sulfate (TGS) detector or an avalanche photodiode model 197-70-72 from Advanced Photonix Inc., Camarillo, Calif. (hereinafter "AP detector"). A large diameter detector, e.g. 16 mm is desirable for increasing light gathering. For this diameter and 110 pF terminal capacitance, an optical path difference (OPD) speed of 0.2 cm/second is suitable. The AP detector incorporates thermoelectric cooling with nitrogen to maintain it at 0° C. A preamplifier in the detector housing should be modified if necessary to increase gain for the low light levels of the present application, e.g. by increasing feedback resistance. A further amplifier, preferably adjustable such as with two stages 0–60 dB and 0–20 dB, may be controlled by the computer through a RS232 port to provide automatic gain switching giving as much gain to the first stage as possible before increasing the gain at the second stage. Maximum signal output of, for example, 10 V peak-to-peak should be consistent with an available A/D.

The interference pattern, and thereby the spectral beam exiting the cranium, is formed of a continuum of spectral wavenumbers that the computer further digitizes into wavenumber increments. The computer is programmed conventionally (or as otherwise desired) for Fourier transformation computations to sort the signal data into ordinary type spectral data representing a plot of intensity vs. wavenumber, frequency or wavelength in spectral increments. Conventional wavenumber calibration is carried out separately, for example with the spectral line of a built-in He—Ne laser in an FTIR, and validated with a known sample (such as polystyrene). Such calibration, not part of the present invention, generally is incorporated into the transformation computations. The further procedures described below are independent of the type of instrument.

Figure 4:
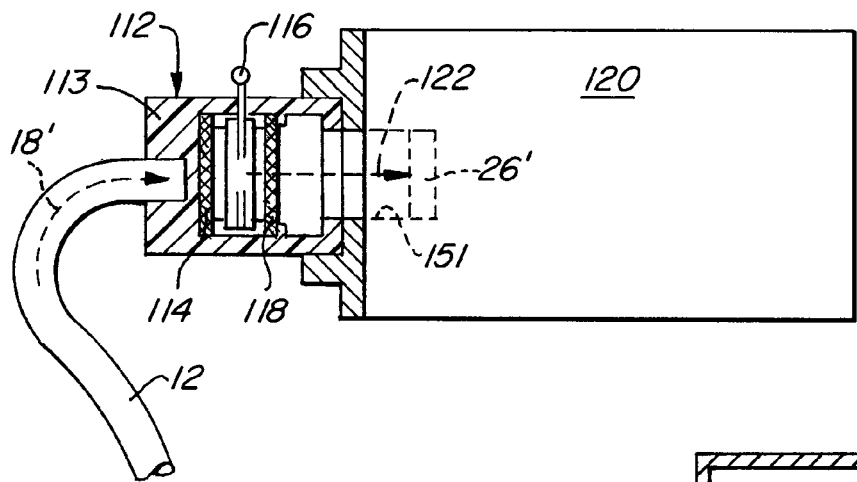
FIG. 4 is a cross-section of a housing for the detector and associated elements of the apparatus of FIG. 1.

Preferably, absorbances (defined below) are computed from intensities. For a reference intensity the probe tip of the first fiber carrier is connected temporarily to the input of a device containing a reference medium to approximate the scattering conditions of a cranium. The details of this device are not critical. One example (FIG. 4) is useful experimentally where attenuation levels have not yet been established. This device 112 has a housing 113 preferably formed of black plastic. Within the housing are, in tandem, a broad spectrum optical diffuser 114, an adjustable iris stop 116 and a second broad spectrum optical diffuser 118 identical to the first. The iris diameter is adjustable, e.g. from 1 mm to 12 mm to adapt the through light to an approximate level of the cranium passage in establishing a setup initially, but thereafter should be held constant for establishment of a particular correlation model (explained below) and thereafter for monitoring. For another example, the iris may be omitted with a diffuser that attenuates the radiation similarly to the cranial configuration actually used.

The input beam 18' (or 18) is passed from the inlet fiber carrier 12 through the reference device 112 to effect an attenuated beam 122 further passed into a housing 120 of the detector (directly as shown, or through a second fiber carrier if used) so as to generate corresponding reference data fed to the computer. Reference intensities are calculated for the spectral range from the reference data, absorbances are computed from the spectral intensities and the reference intensities, and the concentrations are computed from the correlation model and the absorbances. The reference intensities $I_0$, are used for computing absorbance A from measured spectral intensity I measurements according to a conventional formula $A=\log_{10}(I_0/I)$.

Figure 5:
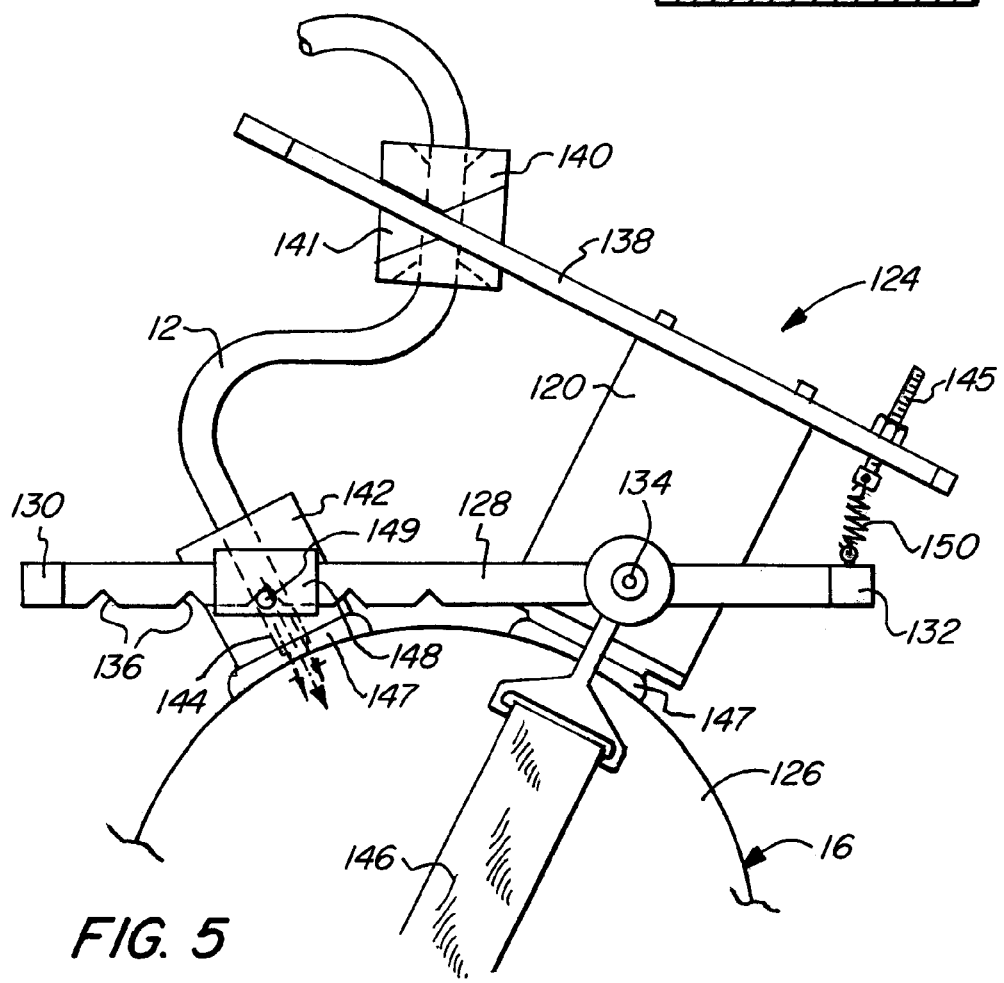
FIG. 5 is an apparatus for placing a light probe and the detector on a cranium.

Any suitable head-mounting apparatus for applying the probe and the detector or the input tip of a second fiber carrier to a test subject's cranium may be used. An example is a device 124 (FIG. 5) that positions the cylindrical housing 120 (without the reference device 112) containing the detector 26' (FIG. 4) so that the detector housing rests directly against the skull 126. A pair of parallel, cantilevered arms 128 (one seen) are affixed apart by a pair of end struts 130, 132. The arms straddle the detector housing which supports a transverse axle 134 on which the arms rotate a short distance from one end strut 132. Along the long portion of the arms from the axle are a series of aligned notches 136 facing toward the subject's cranium 16. A plate 138 is attached to the outer end of the detector housing. A strain relief retainer 140 supports the input fiber carrier 12 passing through the plate, the retainer having angular slots 141 at the plate to allow flexibility in orientation. Another strain relief mount 142 for the probe tip 144, with some slack in the fiber carrier between mounts, is attached to a rod 149 that can be positioned across the arms in a selected pair of notches. The rod is retained on the arms with a spring loaded detent clip 148 over each arm. An extension spring 150 is stretched between the plate 138 and the strut 132 that is on the opposite side of the axle 134 from the probe mount 142, with a threaded adjuster 145 for spring tension. An elastic strap 146 attached to the axle ends passes under the subject's chin to secure the device to the cranium, with the detector housing held against the cranium with the strap. The fiber probe tip 144 on the cantilever is urged against the skull by the extension spring. Disposable, pressure sensitive foam gaskets 147 mounted respectively on the detector housing and the probe mount allow conformity to the cranium and provide a barrier to stray light. Such a device allows adjustment of the spacing between the inlet probe and the detector, and provides a range of tilt angles to accommodate the natural curvature of the skull, while independently maintaining the probe and detector to the skull. For stability and convenience, the device may be suspended from overhead with a counterbalance to neutralize its weight.

Other means for passing the radiation into and out of the cranium may be used. For example, the inlet probe and exit probe or detector may be held with external supports in place of a head bracket. In such a case fiber carriers may not be necessary.

To allow only the scattered light from a well-defined exit site on a brain to be collected, a light pipe 151 (FIG. 4) should be disposed in the entrance of the AP detector housing 120 between the detector surface and the cranium. This pipe, e.g. formed in an inside wall of the housing 120 as shown, should be polished (e.g. aluminum) and of minimal practical length such as 3 mm to position the face of the detector this distance above the cranium. Pipe diameter should be equal to or slightly less than the detector diameter, e.g. 5.9 mm for a 6 mm detector.

Generally the instrument computer may be used, such as a standard PC that is incorporated by the manufacturer of the instrument and has conventional programming to convert data signals to intensity and thence, usually, to absorbance. In the case of FTIR, the time-varying spectral data are treated by matrix operations, in which the signal data are a vector and matrix filters are applied to the vector for the transformation into the intensity data which is a vector. A typical computation system for Fourier transform is taught in the aforementioned textbook by P. R. Griffiths and J. A. de Haseth, particularly pages 81–120, incorporated herein by reference. The computer programming incorporated with the instrument also may deal with calibration, correction for drift, smoothing, determination and subtraction of background, location of peaks, and the like.

The same computer is used advantageously for further computations needed for the present invention. The present programming may be effected with a conventional language such as "C++" or Visual Basic™ from Microsoft. Adaptations of the programming for the present invention from the descriptions and flow charts herein will readily be recognized and achieved by those skilled in the art. The flow charts illustrate method and means for carrying out the invention.

Figure 6:
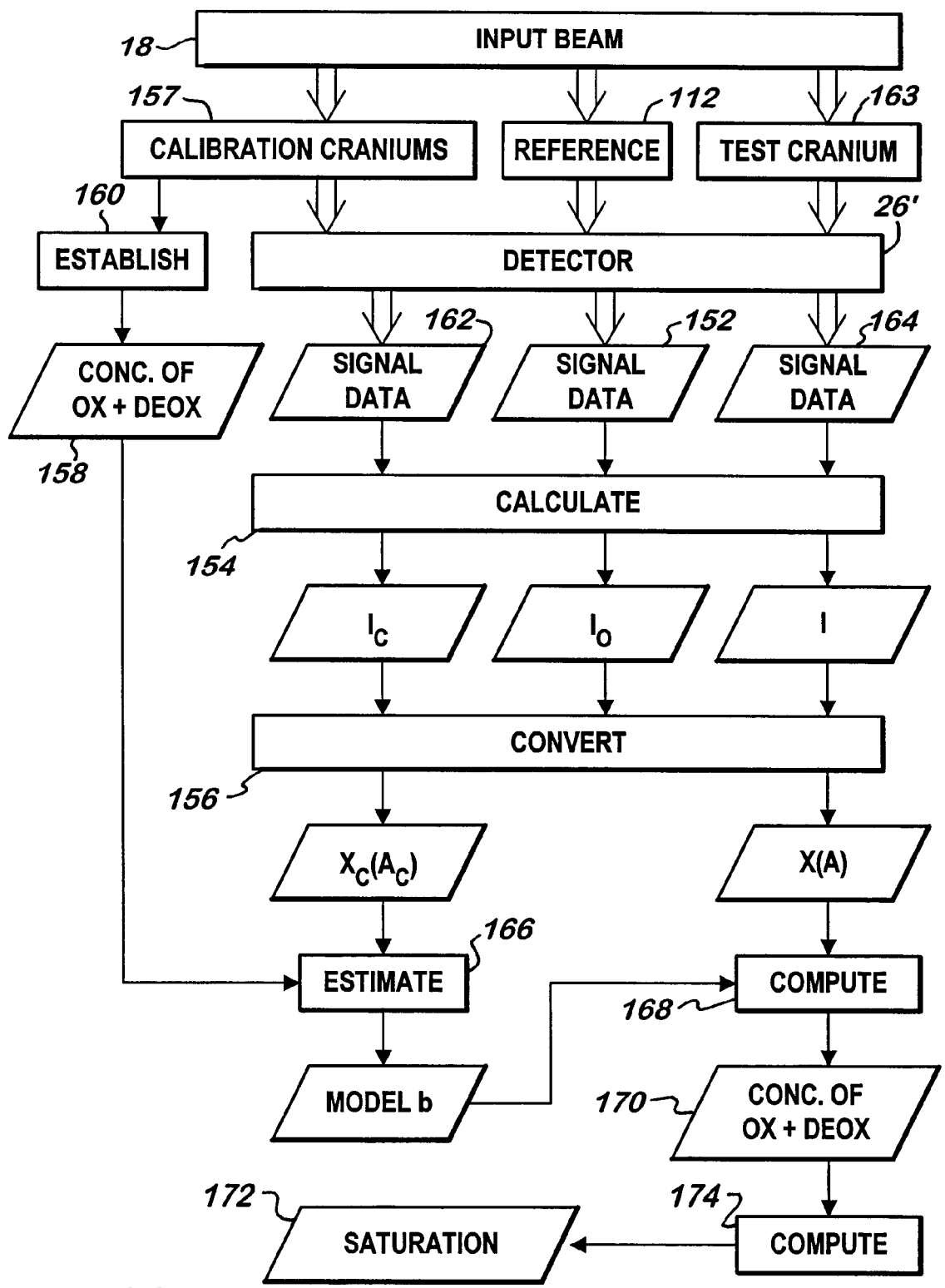
FIG. 6 is a flow chart for calculations in accordance with the invention.

A reference run is made (FIG. 6) by passing the input beam 18 through the reference device 112 to the detector 26' that generates signal data 152 from which is calculated 154 a reference intensity $I_0$. This run is made at least once, and preferably again at the time of each normal run or series of runs.

A calibration procedure is carried out to determine a matrix model correlating intensities, preferably in the form of absorbance values, with measured data such as concentrations of oxy and deoxy hemoglobin. Such data are measured conventionally such as by withdrawing blood from the cranium with a catheter and measuring oxygen content with a standard blood gas analyzer. Data are collected for the brains of a multiplicity of subjects having different oxygenations and total amounts of hemoglobin, for example for 100 or more data sets. The subjects should be the same type as each other and as for future applications, e.g. human or dog craniums. The measured data are effectively in the form of a data matrix $Y_c$ with the vertical axis listing the measured data and the horizontal axis representing the several biomolecular compounds. (The subscript "c" refers to the calibration measurements.) For example, for 100 data sets and 2 hemoglobin concentrations (oxygenated and deoxygenated), the matrix is 100×2. If other data are added such as pH and partial pressure of $CO_2$, the matrix may be 100×4. In the further example illustrated below, a 100×2 matrix is considered. (The term "matrix" and its array form of data are used herein conceptually and in equations to denote mathematical operations; for computer operations the data need not be stored or presented in a matrix array.)

Spectral intensity data are taken with the selected instrument by passing the radiation through each of a set of "calibration" craniums 157 of people or other animals. Concentrations 158 of the desired constituents (e.g. oxy and deoxy hemoglobin) are measured or otherwise established 160. For each of the calibration craniums, the input beam is directed into the cranium, at the same general time of measurement of the concentrations so as to ensure correlation. The spectral detector 26' (for the example of FTIR) is positioned to be receptive of the attenuated radiation from the exit site from the organ so as to generate signal data 162 representative of spectral distribution of the attenuated radiation. Spectral intensities $I_c$ are calculated 154 from the signal data over the spectral range, and converted 156 to absorbance values $A_c$. The absorbances are effectively in the form of an "intensity" matrix $X_c$ wherein intensities preferably are represented by absorbances. Each row in the matrix is effectively a spectrum across the horizontal axis representing wavelength increments which may be digital increments (e.g. pixels). For the 100 spectra (from one or more runs on various subjects) and 401 pixels (e.g. representing 700 to 1100 nm with 1 nm steps), this matrix is 100×401.

A matrix model b is desired for statistically correlating $X_c$ and $Y_c$ in a matrix formula $Y_c=X_cb+e$ where b is a 401×2 matrix of correlation constants and e is a 100×2 error matrix to be minimized. The model represents a statistical correlation and is not dependent on, and does not involve any theoretical physical relationship between concentrations and spectral measurements. A conventional regression technique may be used, such as linear regression, multiple linear regression, stepwise regression, partial least squares regression or principal component regression. Preferably, a biased regression procedure is used to estimate 166 the matrix model b with $b^\sim=(X_c^+)Y_c$ where b is approximated by $b^\sim$ and $X_c^+$ is the inverse of $X_c$, such that e is minimized. The procedure may conventionally utilize a rank r which is a selected number of independent variations in $X_c$ which should be greater than 2, for example 6.

A problem arises from the different geometries of different subjects, and even from time to time with the same subject, in obtaining spectral intensities. Such differences manifest as is variations in path length which cannot be measured directly with confidence. The result can be a model b that correlates $X_c$ and $Y_c$, with less accuracy than may be desired. A solution is to utilize a path-length scaling vector $l_c$ having a number of scaling elements equal to the number of subjects in the data set, e.g. 10 for the above example of a 100×2 matrix for $Y_c$ with 10 spectra from each of 10 subjects. If the same subject is measured multiple times each with slightly different mounting of the cranium-coupling optics, the data should be treated as multiple subjects.

The elements define a diagonal scaling factor in the form of a matrix $L_c$ with the scaling elements in the diagonal and zeros elsewhere. For practical computations the elements are for each of the 10 subjects. If there were no correction, the diagonal elements each would be equal to one (unity matrix). To apply the correction, the calibration matrix is modified to $L_c Y_c = X_c b + e$ so as to apply the scaling factor to the concentrations. Alternatively, as a mathematical equivalent, the calibration matrix formula is modified to $Y_c = L_c^{-1} X_c b + e$, where $L_c^{-1}$ is a diagonal matrix that is inverse of $L_c$, so as to scale the spectral data in $X_c$. A statistical regression procedure then estimates the scaling elements $l_c$ along with the determination of b such that the residual matrix e is minimized, thereby providing a more accurate matrix model b.

Any applicable regression procedure may be used. To implement the regression, the first (or any other) scaling element may be set to one, and the remaining elements are estimated along with b. One approach is to start by setting all scaling elements to one, calculate b conventionally, and then update the elements and b using Simplex optimization until e is sufficiently minimized.

A preferable approach is to start with all scaling elements equal to one and calculate a preliminary $b^{(0)}$ from $Y_c = X_c b^{(0)} + e$, in the desired manner (e.g. biased regression), and calculate a fitted value $Y^\sim_c$ for the reference data matrix from $Y^\sim_c = X_c b^{(0)}$. Each of $Y_c$ and $Y^\sim_c$ are partitioned in pairs of corresponding submatrices $Y_c^i$ and $Y^{\sim i}_c$ where i=1,2,3, ... n, each i corresponding to a subject/experiment run during calibration, there being n such sets (e.g. 10). The pairs are unfolded into two long vectors, and each unfolded version of $Y^\sim_c{}^i$ is regressed against that of $Y_c^i$ to yield a slope. The slope serves as the next estimate of a corresponding new scaling factor $l_c^i$. After all of the new scaling factors have been estimated, a normalized version of $X_c$ is calculated as:

$$X_c^{(1)} = \begin{bmatrix} X_c^1 \\ X_c^2 \cdot l_c^1 / l_c^2 \\ \vdots \\ X_c^n \cdot l_c^1 / l_c^n \end{bmatrix}$$

where each $X_c^i$ contains rows of spectral data. A new regression matrix $b^{(1)}$ is estimated from $Y_c = X_c^{(1)} b^{(1)} + e$, and the process is repeated until e is minimized. This should converge rapidly to a suitable model b, especially with a large number of subjects, e.g. greater than 10.

In an application for monitoring a subject, one or preferably (for accuracy) a series of runs is made on the subject, e.g. on a test cranium 163. The detector effects signal data 164 from which are calculated 154 intensities I, preferably for a statistically significant number of sets of intensities in a short time, e.g. 10 seconds. Upon conversion 156 to absorbance A, if 50 runs are made for the spectral range of 401 pixels, an intensity matrix X of absorbances will be a 50×401 matrix. The desired concentrations 170 of constituents such as oxy and deoxy hemoglobin, and/or other data for the brain, are computed 168 from the matrix formula Y=Xb where b is approximated by $b^{18}$ and Y is a 50×2 matrix with two columns, one each for the two hemoglobins. Each column may be averaged in a small time window to provide the two concentrations. With two more constituents of is interest, Y will be a 50×4 matrix.

Computed concentrations of oxy and deoxy hemoglobin and/or other components from the model b also will be dependent on exact effective optical path length in the brain (or other organ), so these concentrations will only be approximate. This path is sensitive to configuration of the subject and the placement of the head-mounting apparatus. Since pathlength is a function of wavelength, spectral peaks cannot be readily quantified. In fact, even the ratio of two peaks used for the purposes of obtaining a ratio of concentrations such as an oxygen saturation would not normally be accurate because of the different pathlengths associated with each peak. However, this dependence of pathlength can be sufficiently well corrected by the multivariate bias regression method outlined above. This correction essentially "flattens" the pathlength dependence on wavelength, but does not provide an absolute measurement. Hence, ratios of concentrations can be accurately determined, although absolute concentrations cannot. Thus, the dependence of path length essentially cancels out in a computation 174 for oxygen saturation 172 which is the percentage of oxy hemoglobin to the total of oxy and deoxy hemoglobin. As this saturation is normally of primary interest, the absolute numbers may not be important and, therefore, the foregoing apparatus and procedures generally should be sufficient.

In cases where absolute concentrations are desired, the foregoing continuous-wave full-spectrum (CWFS) system may be combined with a second system of measurement to provide correction for variations in path length. Such improvements will enable the quantitation of hemoglobin or of cytochrome aa3. One such system utilizes amplitude modulation of radiation having at least one discrete (narrow band) spectral wavelength, preferably at least two such wavelengths, and more preferably as many as practical, e.g. four to six. Phase shift for the modulation is utilized to compute path lengths for the several wavelengths, from which path length is computed for each spectral increment. Such a system is disclosed in an article "Low-Cost Frequency-Domain Photon Migration Instrument for Tissue Spectroscopy, Oximetry, and Imaging" by Yunsong Yang, Hanli Liu, Xingde Li and Britton Chance, Opt. Eng. 36 (5) 1562–1569 (May 1997). A similar system is described in an article "A Homodyne Frequency-Domain Instrument—I&Q Phase Detection System" by H. Y. Ma, C. W. Du and B. Chance, Opt. Eng. 36 (5) 1562–1569 (May 1997). The portions of each of these articles that are relevant to a modulated laser system and its use for calculating phase shift are incorporated herein by reference. The present system is summarized below, with details being set forth in these references. Other aspects of the technology of these articles are replaced or modified by the improvements set forth herein.

Figure 7:
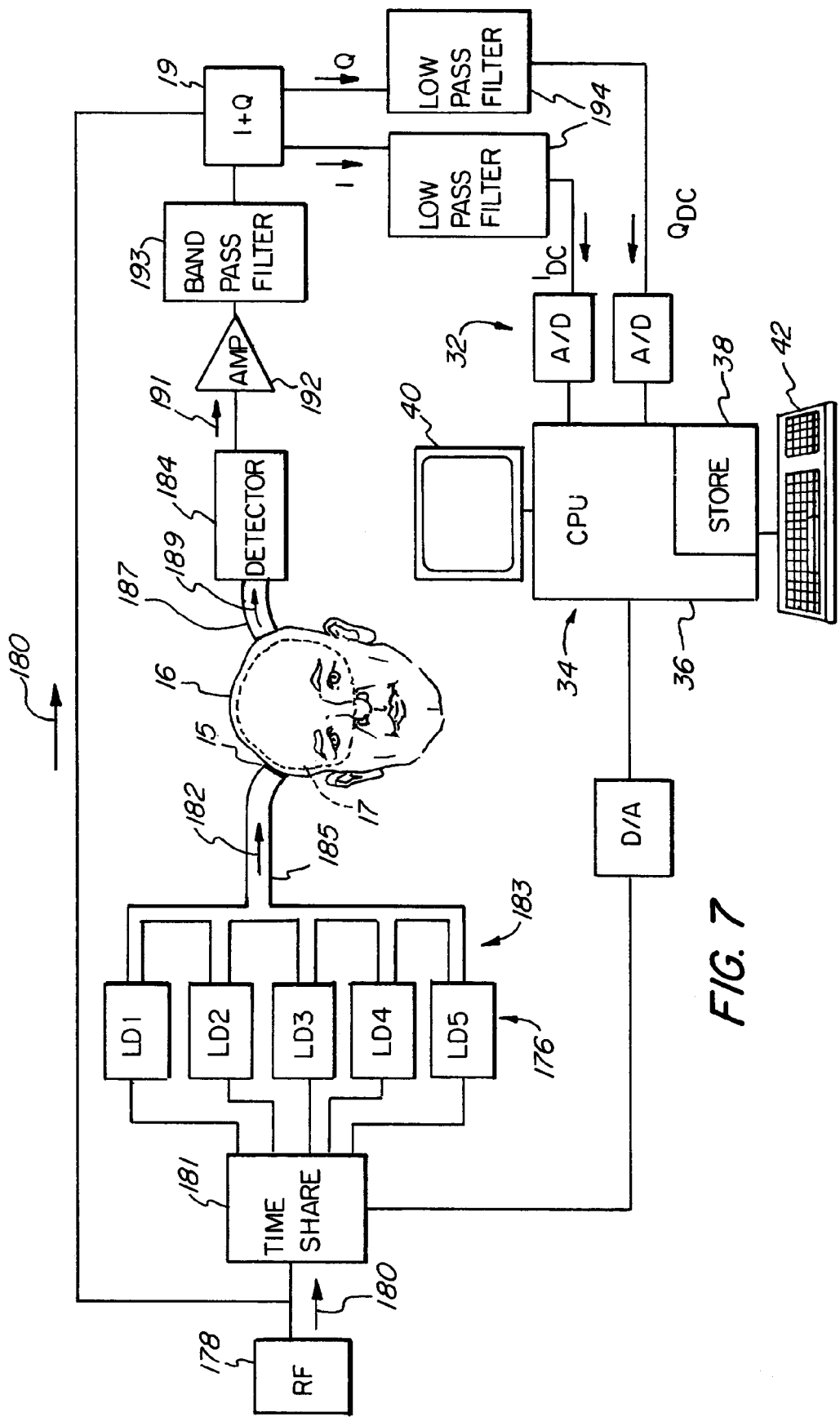
FIG. 7 is a block diagram of a system for determining path length to be used in accordance with the invention.
Figure 8:
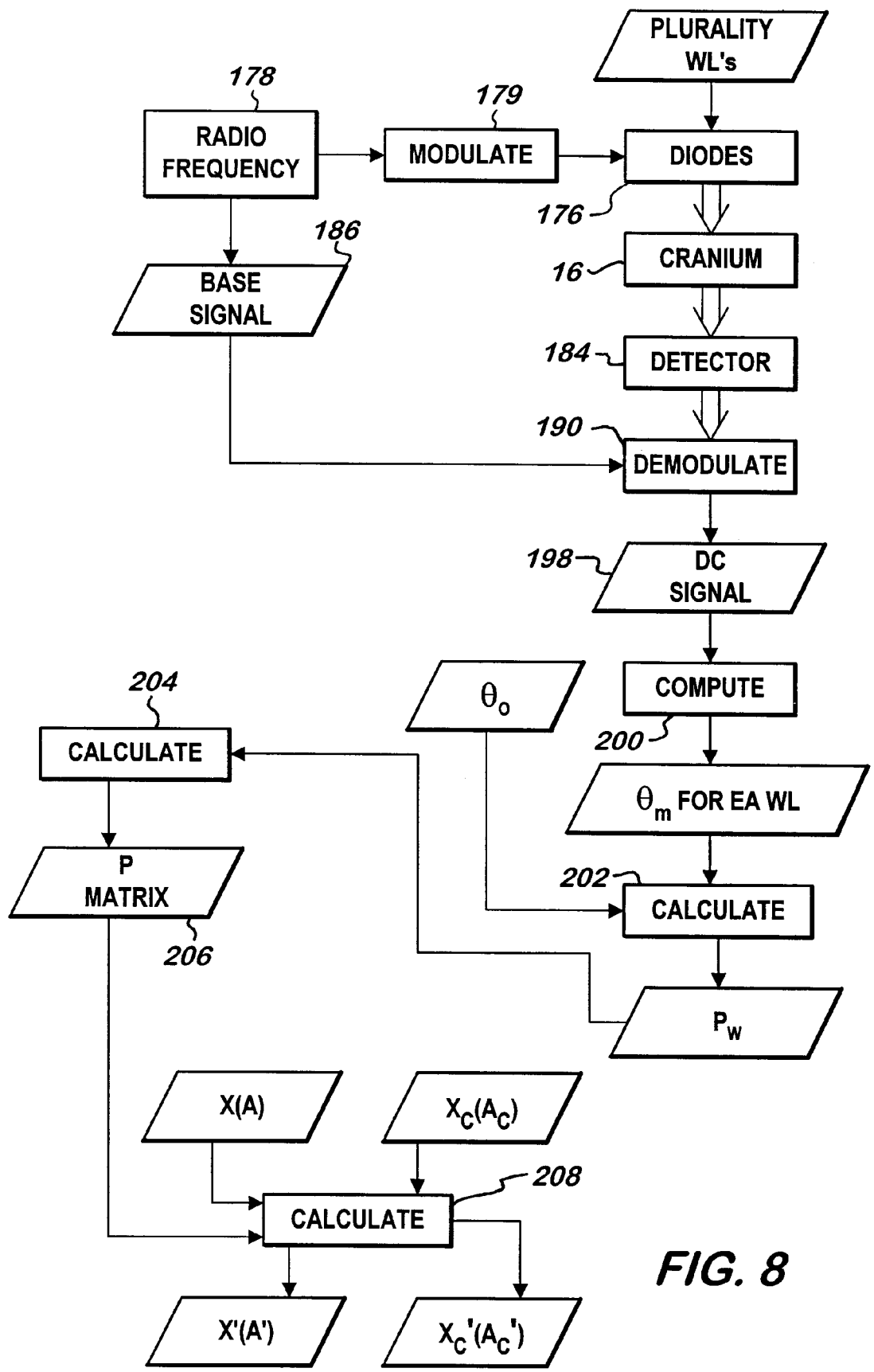
FIG. 8 is a flow chart illustrating electronic operations and calculations in accordance with the invention as shown in FIG. 7.

In this system, one or more laser diodes 176 (FIGS. 7, 8) provide radiation with several discrete (narrow band) wavelength components in the desired range (e.g. 700–1100 nm), for example 754, 786, 810 and 830 nm from diode model numbers LT031MD, LT027MD, LT017MD and LT015MD respectively from Sharpe Electronics, and 830 nm with Sanyo diode model number DL6033-101. (FIG. 7 illustrates 5 diodes.) An oscillator circuit 178 applies a continuous radio frequency (RF) signal 180 generally between 100 MHz and 300 MHz, e.g. about 140 MHz, to each of the diodes to amplitude-modulate 179 the emissions. The RF signal is passed through a time share switching circuit 181 controlled by the computer 34 to pass the RF signal sequentially to the diodes at a cycle rate of, for example, 10 Hz. Alternatively the modulation frequencies for the several diodes may have small frequency separations (e.g. 0.1 MHz) with omission of the switching circuit. Either of these or any other approach may be used to provide separation of the signals for processing for the different wavelengths.

The diode emissions are coupled into a combined beam or beams 182 of discrete radiation which may be achieved by combining fibers 183 from each diode into a total bundle 185. The combined beam is directed into the fiber carrier either of the same head-mounting apparatus as for the aforedescribed CWFS system or a separate apparatus with the same geometry and positioning on the cranium 16 to duplicate the path length. The diode light may be applied simultaneously or in quick succession with the continuous a wave radiation into the fiber carrier with a beam splitter, for simultaneous or nearly simultaneous measurements. The radiation 187, modified by the organ, is received (optionally via a fiber carrier 189) by a radiation detector 184 which may be the same as used for the CWFS system, or may be selected for the discrete radiation such as an avalanche photodiode detector.

Signals 191 from the detector are amplified through an amplifier 192 (which may be a series of amplifiers) and passed through a band pass filter 193 to remove noise outside of the selected radio frequency. An "in-phase and quadrature phase" (I&Q) demodulator circuit 190 receives and compares signals from the detector with the base radio frequency signal 186 to provide outputs I(t) and Q(t) (where t is time) which are low-pass filtered 194 into DC signals $I_{DC}$ and $Q_{DC}$ (198) as described in Yang et al. These signals are A/D converted 32 and fed to the processor 36. A measured phase $\theta_m$ and amplitude $A_m$ are computed 200 from the converted DC signals for each optical frequency utilizing equations set forth in Yang et al.:

$$\theta_m = \tan^{-1}(Q_{DC}/I_{DC}) \quad \text{Eq. 1}$$

$$A_m = (Q_{DC}^2 + I_{DC}^2)^{1/2} \quad \text{Eq. 1a}$$

As further set forth in the aforementioned articles, amplitude and phase are related to the absorption coefficient $\mu_a$ and the scattering coefficient $\mu_s$ by equations (for an infinite, homogeneous medium):

$$\theta_m - \theta_0 = r[(w^2 + v^2\mu_a^2)^{1/2} 3 1 \, v\mu_a]^{1/2}/(2v/3\mu_s)^{1/2} \quad \text{Eq. 2}$$

$$A_m/A_0 = (3\mu_s/4\pi vr) \exp\{-r[(w^2+v^2\mu_a^2)^{1/2}+v\mu_a]^{1/2}/(2v/3\mu_s)^{1/2}\} \quad \text{Eq. 3}$$

where $\theta_0$ is input phase of input radiation RF modulation without the organ, $A_0$ is amplitude of the input radiation to the organ, r is spacing between the organ input and output sites (FIG. 1), w=2πf where f is the RF modulation frequency, and v is the speed of light in the organ. For speed of light, an accepted index of refraction of 1.4 for tissue may be used. Other equations that reasonably relate the relevant variables may be used and should be deemed equivalent for the purposes of this invention.

Figure 9:
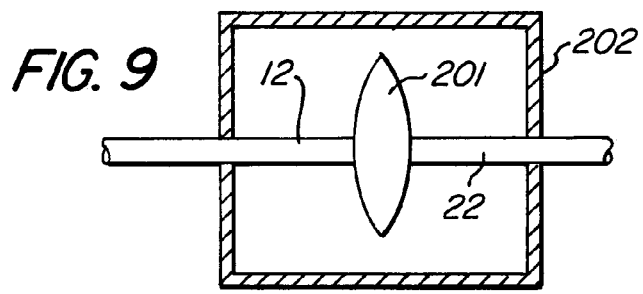
FIG. 9 is a cross sectional view of a housing for a filter for it use with the invention of FIG. 1.

As indicated in Yang et al., with the scattering coefficient $\mu_s$ being unknown, Eqs. 2 and 3 may be solved iteratively for the absorption coefficient without determination of input values $\theta_0$ and $A_0$. For greater accuracy, these values may be determined by measurement of an amplitude $A_{nd}$ and phase $\theta_{nd}$ with a neutral density filter 201 (FIG. 9) positioned between the input fiber carrier 12 and the output carrier 22. The filter and fiber connections should be in an enclosure 203 to keep out stray light. The input phase is equal to the measured phase, i.e. $\theta_0 = \theta_{nd}$, and the input amplitude is $A_0 = A_{nd}/T$ where T is the transmission efficiency of the filter. The filter has a predetermined optical density OD generally supplied by the manufacturer. $A_0$ and $\theta_0$ should be measured before each use (e.g. when the instrument is turned on) or more often depending on instrument stability.

An effective optical path length $P_w$ in the cranium for each diode wavelength w is calculated 202 from the phase shift $\theta_0 - \theta_0$, with a conventional scattering formula $P_w = (\theta_m - \theta_0) v/2\pi f$ where v is speed of light in the organ and f is the modulation frequency. The several measured values of $P_w$ for the different diode wavelengths are fitted to a curve (quadratic generally should be sufficient) which will be a relatively smooth from which a spectral path length P is calculated 204 for every wavelength increment (e.g. pixel). This determination is repeated for each of the monitoring runs on a subject. In the case of 50 runs on a subject being monitored, this produces a 50×401 P matrix 206. This procedure also is effected for the calibration runs which, in the case of 100 subjects for calibration, effects a 100×401 matrix $P_c$. If only one discrete wavelength is implemented, the "calculation" of path lengths P for all relevant wavelengths can be known since the multivariate bias regression method had already "flattened" pathlength dependence, leaving only an offset to be determined. A single diode channel can then provide the offset.

Results of time domain spectroscopy show that variations of pathlength with wavelength are smooth. Consequently, reconstructing this curve with a small number (say 3 to 5) of discrete wavelength channels is practical. This information can be used to help improve estimation of the offset.

According to scattering theory, spectral intensity is exponentially dependent on path length P in a turbid medium such as a brain, so absorbance is directly proportional to P. Based on this, a normalized matrix X' (A') of absorbances A' is calculated 208 from X'=X/P point by point. Similarly a matrix $X_c'$ ($A_c'$) of normalized absorbances $A_c'$ is calculated from $X_c'=X_c/P_c$ for calibration. The normalized matrices for absorbance are used in place of the original intensity (absorbance) matrices $X_c$ and X for $A_c$ and A respectively in the foregoing computations (FIG. 6) for the correlation matrix model b and the concentrations (and/or other data) Y. These concentrations, such as for oxy and deoxy hemoglobin, will be significantly more accurate than with non-normalized matrices, and may be used directly.

Alternatively, the phase modulation technology, especially with the reconstructed path length curve vs. wavelength obtainable from 3 to 5 channels, may be used to correct a steady state spectrum itself. Thus reliance on the multivariate bias regression method would become unnecessary since the entire spectrum would be renormalized to correct pathlengths directly.

Other means and methods may be used for ascertaining path length with sufficient accuracy for the normalization, such as photon time-of-flight measurements.

The use of an FTIR instrument, as opposed to for example a CCD or other similar device, enables operation in ambient light without the need to take extreme measures to shield the detector or the organ. An FTIR instrument also has much higher light through-put, thus improving the signal to noise ratio by as much as a factor of ten. The foregoing system and method as applied to monitoring oxygen saturation of hemoglobin has been tested on dogs and humans with levels of success that were surprising to the inventors.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. A method of monitoring one or more selected molecular constituents in an animal organ, with a spectrometric instrument that includes a source of an input beam of infrared radiation having a substantially full spectrum in a spectral range that includes absorbance wavelengths of the selected constituents, and a spectral detector receptive of such radiation to generate representative signal data, the method comprising steps of directing the input beam into an animal organ at an input site, wherein the radiation is attenuated by constituents of the organ including the selected constituents, positioning the spectral detector so as to be receptive of the attenuated radiation from an exit site from the organ so as to generate signal data representative of spectral distribution of the attenuated radiation, calculating spectral intensities over the spectral range from the signal data, converting spectral intensities to absorbances, and computing concentrations of the selected constituents from the absorbances and from a predetermined statistical correlation model relating such concentrations and absorbances.

2. The method of claim 1 wherein, to predetermine the correlation model, the method further comprises steps of:
   effecting the steps of directing the input beam, positioning the spectral detector and calculating spectral intensities, for a plurality of organs of a same type with each organ having established concentrations of the selected constituents; and
   statistically determining the correlation model from the concentrations and corresponding intensities.

3. The method of claim 2 wherein the step of statistically determining includes applying a scaling factor to the concentrations such that each of the concentrations is scaled, wherein the scaling factor is determined statistically along with the correlation model.

4. The method of claim 1 wherein the source and the detector are disposed so that the radiation passes through a cranium, and the organ is a brain, whereby the radiation is attenuated by brain constituents.

5. The method of claim 1 wherein the spectral range is from about 700 nm to about 1100 nm, and the select molecular constituents comprise oxygenated hemoglobin and de-oxygenated hemoglobin.

6. The method of claim 1 wherein the instrument is an infrared Fourier transform spectrometric instrument, the source comprises a time varying interference pattern, and the spectral detector comprises a photodetector.

7. The method of claim 1 wherein the instrument is a dispersion instrument such that the source is a steady source of infrared radiation, and the spectral detector comprises a dispersion element receptive of the attenuated radiation to effect dispersed radiation, and a photodetector receptive of the dispersed radiation to effect the spectral signal data.

8. The method of claim 1 wherein the one or more selected constituents is a plurality of selected constituents.

9. The method of claim 8 wherein the plurality of selected constituents comprise at least two bimolecular compounds.

10. The method of claim 9 wherein the biomolecular compounds comprise oxygenated hemoglobin and de-oxygenated hemoglobin.

11. The method of claim 10 wherein the organ is a cranium, and the radiation is attenuated by brain constituents including the oxygenated hemoglobin and deoxygenated hemoglobin.

12. The method of claim 10 further computing saturation level of oxygenated hemoglobin relative to a total of the oxygenated hemoglobin and de-oxygenated hemoglobin, wherein the saturation level is independent of path length of the radiation to the spectral detector.

13. The method of claim 10 wherein the instrument is an infrared Fourier transform spectrometric instrument, the source comprises a time varying interference pattern, and the spectral detector comprises a photodetector.

14. The method of claim 13 wherein the spectral range is from about 700 nm to about 1100 nm.

15. The method of claim 14 wherein, to predetermine the correlation model, the method further comprises steps of:
   effecting the steps of directing the input beam, positioning the spectral detector and calculating spectral intensities, for a plurality of organs of a same type with each organ having established concentrations of the oxygenated hemoglobin and de-oxygenated hemoglobin; and
   statistically determining the correlation model from the concentrations and corresponding intensities.

16. The method of claim 15 wherein the step of statistically determining includes applying a scaling factor to the concentrations whereby each of the concentrations is scaled, wherein the scaling factor is determined statistically along with the correlation model.

17. The method of claim 15 further comprising computing saturation level of oxygenated hemoglobin relative to a total of the oxygenated hemoglobin and de-oxygenated hemoglobin, whereby the saturation level is independent of path length of the radiation to the spectral detector.

18. The method of claim 17 wherein the organ is a cranium, and the radiation is attenuated by brain constituents including the oxygenated hemoglobin and de-oxygenated hemoglobin.

19. The method of claim 1 wherein the step of converting comprises passing the input beam through a reference medium to the spectral detector to generate corresponding reference data, calculating reference intensities over the spectral range from the reference data, and computing absorbances from the spectral intensities and the reference intensities.

20. The method of claim 1 wherein, to predetermine the correlation model, the method further comprises steps of:
   effecting the steps of directing the input beam, positioning the spectral detector, calculating spectral intensities, and converting intensities to absorbances, for a plurality of organs of a same type with each organ having established concentrations of the selected constituents; and
   statistically determining the correlation model from the concentrations and corresponding absorbances.

21. The method of claim 20 wherein the step of statistically determining includes applying a scaling factor to the concentrations whereby each of the concentrations is scaled, wherein the scaling factor is determined statistically along with the correlation model.

22. The method of claim 1 further comprising the steps of ascertaining a path length of the radiation in the organ between the input site and the exit site, and dividing each absorbance for each spectral increment by the path length to effect normalized absorbances, the concentrations being computed from the correlation model and the normalized absorbances.

23. The method of claim 22 wherein the input beam is directed into the organ at the input site, and the step of ascertaining comprises:

effecting a further beam of input discrete radiation comprising at least one discrete wavelength component in the spectral range, each wavelength component being modulated with a radio frequency signal;

directing the further beam into the organ at the input site wherein the discrete radiation is modified by the organ;

positioning a radiation detector to be receptive of the modified radiation from the exit site to generate corresponding detector signals;

determining a phase shift between the radio frequency signal and the corresponding signals, and thereby between the input discrete radiation and the modified radiation for each discrete wavelength;

calculating, from each phase shift, correspondingly at least one effective path length of the discrete radiation in the organ between the input site and the exit site; and computing, from the at least one effective path length, a spectral path length for each spectral increment in the spectral range, each absorbance for each spectral increment being divided by an increment path length for that spectral increment to effect normalized absorbances.

24. The method of claim 23 wherein the input discrete radiation comprises a plurality of discrete wavelength components in the spectral range, wherein a corresponding plurality of effective path lengths are calculated for the computing of the increment path length for each spectral increment.

25. An apparatus for monitoring one or more selected constituents in an animal organ, comprising:

a spectrometric instrument including a source of an input beam of infrared radiation having a substantially full spectrum in a spectral range that includes absorbance wavelengths of the selected constituents, and a spectral detector receptive of radiation to generate representative signal data;

directing means for directing the input beam into an animal organ at an input site wherein the radiation is attenuated by constituents of the organ including the selected constituents;

positioning means for positioning the spectral detector so as to be receptive of the attenuated radiation from an exit site from the organ to generate signal data representative of spectral distribution of the attenuated radiation; and computing means for calculating spectral intensities over the spectral range from the signal data, for converting spectral intensities to absorbances, and for computing concentrations of the selected constituents from the absorbances and from a predetermined statistical correlation model relating concentrations and absorbances.

26. The apparatus of claim 25 wherein the source and the detector are disposed cooperatively wherein the radiation can pass through a cranium, and the organ is a brain, wherein the radiation is attenuated by brain constituents.

27. The apparatus of claim 25 wherein the instrument is an infrared Fourier transform spectrometric instrument, the source comprises a time varying interference pattern, and the spectral detector comprises a photodetector.

28. The apparatus of claim 25 wherein the input beam is directed into the organ at an input site, the apparatus further comprises:

means for effecting a further beam of input discrete radiation comprising at least one discrete wavelength component in the spectral range, each wavelength component being modulated with a radio frequency signal;

means for directing the further beam into the organ at the input site wherein the discrete radiation is modified by the organ;

means for positioning a radiation detector to be receptive of the modified radiation from the exit site to generate corresponding detector signals; and means for determining a phase shift between the radio frequency signal and the corresponding signals, and thereby between the input discrete radiation and the modified radiation for each discrete wavelength; and the computing means further comprises:

means for calculating, from each phase shift, a corresponding effective path length of the discrete radiation in the organ between the input site and the exit site;

means for computing, from the at least one effective path length, a spectral path length for each spectral increment in the spectral range;

means for dividing each absorbance for each spectral increment by the path length for that spectral increment to effect normalized absorbances, the concentrations being computed from the correlation model and the normalized absorbances.

* * * * *